(12) United States Patent
Nazabal et al.

(10) Patent No.: US 7,943,387 B2
(45) Date of Patent: May 17, 2011

(54) DIRECT MASS SPECTROMETRIC ANALYSIS OF AGGREGATES OF THERAPEUTIC PROTEINS

(75) Inventors: Alexis Nazabal, Zürich (CH); Ryan Jay Wenzel, Melrose, MA (US)

(73) Assignee: Covalx AG, Zurich (CH)

( * ) Notice: Subject to any disclaimer, the term of this patent is extended or adjusted under 35 U.S.C. 154(b) by 0 days.

(21) Appl. No.: 12/448,313

(22) PCT Filed: Dec. 17, 2007

(86) PCT No.: PCT/EP2007/064056
§ 371 (c)(1),
(2), (4) Date: Jul. 17, 2009

(87) PCT Pub. No.: WO2008/074769
PCT Pub. Date: Jun. 26, 2008

(65) Prior Publication Data
US 2010/0022013 A1    Jan. 28, 2010

(30) Foreign Application Priority Data
Dec. 18, 2006 (EP) .................................. 06126353

(51) Int. Cl.
*G01N 33/15* (2006.01)
(52) U.S. Cl. .................... 436/86; 436/2; 436/8; 436/63; 436/173; 436/176
(58) Field of Classification Search .................. None
See application file for complete search history.

(56) References Cited

U.S. PATENT DOCUMENTS
2006/0271306 A1    11/2006 Dobson et al.

FOREIGN PATENT DOCUMENTS
WO    2005/045442    5/2005
WO    2006/116893    11/2006

OTHER PUBLICATIONS

Cleland, Jeffrey L. et al. "A specific molar ratio of stablizer to protein is required for storage stability of a lyophilized monoclonal antibody." Journal of Pharmaceutical Sciences (2001) 90 310-321.*
"Monoclonal Antibody Production." A Report of the Committee on Methods of Producing Monoclonal Antibodies by the Institute for Laboratory Animal Research, National Research Council, Washington, DC 1999.*
Nazabal, Alexis et al. "Immunoassays with direct mass spectrometric detection." Analytical Chemistry (2006) 78 3562-3570.*

(Continued)

*Primary Examiner* — Yelena G Gakh
*Assistant Examiner* — Christopher A Hixson
(74) *Attorney, Agent, or Firm* — Wenderoth, Lind & Ponack, L.L.P.

(57) ABSTRACT

The invention relates to a method of using high-mass matrix assisted laser desorption-ionization (MALDI) mass spectrometry for the quantitative analysis of the amount of aggregation (dimers, trimers or multimers) of antibodies or other therapeutic proteins in purified pharmaceutical samples or complex biological matrices, as well as to the use of this method for characterization of antibodies, drug development and quality control of therapeutic proteins, including automated high throughput applications.

12 Claims, 4 Drawing Sheets

OTHER PUBLICATIONS

Wenzel, Ryan J. et al. "Comparison of sensitivity and saturation of MALDI-ToF detectors for high mass ions." Proceedings of the 54th ASMS Conference on Mass Spectrometry; Seattle, May 2006.*

International Search Report issued Mar. 10, 2008 in PCT/EP2007/064056 of which the present application is the U.S. National State.

PCT Written Opinion issued Mar. 10, 2008 in PCT/EP2007/064056.

Farmer et al., "Assessing the Multimeric States of Proteins: Studies Using Laser Desorption Mass Spectrometry", Biological Mass Spectrometry, vol. 20, pp. 796-800 (1991).

Farmer et al., "Mass Discrimination in Matrix-assisted Laser Desorption Ionization Time-of-Flight Mass Spectrometry: a Study Using Cross-linked Oligomeric Complexes", Journal of Mass Spectrometry, vol. 30, pp. 1245-1254 (1995).

Gerard Bolbach, "Matrix-Assisted Laser Desorption/Ionization Analysis of Non-Covalent Complexes: Fundamentals and Applications", Current Pharmaceutical Design, vol. 11, pp. 2535-2557 (2005).

* cited by examiner

DIRECT MASS SPECTROMETRIC ANALYSIS OF AGGREGATES OF THERAPEUTIC PROTEINS

FIELD OF THE INVENTION

The present invention relates to a method of analysis the aggregation of therapeutic proteins and the quantification of aggregation using High-Mass MALDI mass spectrometry on intact ions from undigested, unfragmented covalently stabilized aggregates of therapeutic proteins such as antibodies or other therapeutics proteins.

BACKGROUND OF THE INVENTION

Identification and characterization of antibodies aggregates or other intermolecular products of antibodies is of major importance as numerous antibodies are used as pharmaceutical products. The analysis of antibodies aggregates or aggregates formed by other therapeutic proteins as a consequence of aging, heat stress, pH stress or host cell expression is of crucial importance to evaluate the stability of these therapeutic molecules.

Aggregation of therapeutic proteins such as antibodies can become a major problem when application to a patient requires a high concentration to achieve therapeutic efficacy. The aggregation of antibodies and other therapeutic proteins has important consequences including decreased activity and solubility. A major consequence of therapeutic protein aggregation is also an increasing immunogenicity that can have consequences for the patients treated.

The aggregation of monoclonal antibodies and other therapeutic proteins is a complex problem to be addressed as the aggregation can affect the proteins differently depending on the type of stress involved. During production, monoclonal antibodies and other therapeutic proteins are submitted to temperature, pressure and pH variations that can lead to aggregations. The analysis of antibodies aggregation is of high interest as this phenomenon has an influence on the binding of these therapeutics on their targets (antigen, receptor, or the like).

Conventional technologies for the analysis of such antibodies aggregates include size exclusion chromatography (SEC), whereby the protein extract containing the antibody aggregate is separated from the monomeric form and collected in liquid phase; near- and far UV circular dichroism analysis, whereby the tertiary structure of monomers and dimers can be evaluated; capillary electrophoresis with sodium dodecyl sulfate (CE-SDS), whereby antibodies aggregates can be characterized distinguishing between covalent and non-covalent aggregation. Using electrospray ionization (ESI) mass spectrometry, it is possible to distinguish between different species of antibody aggregates pre-fractionated by size exclusion chromatography combined with reverse phase chromatography (SEC/rp-HPLC) (Remmele, R. et al., J. Pharma. Sci. 95:126-145 (2005)). This ESI mass spectrometric analysis does not allow a quantitative analysis of the amount of aggregation of a sample as this analysis has to be applied to highly purified fractions of the aggregated sample.

MALDI mass spectrometry has been used for the analysis of intact non-covalent protein complexes. Many particular methodologies including specific matrix and laser combinations, accumulation of "first shot" spectra, modification of pH, selected solvent conditions during sample preparation, and use of crosslinking reagents to stabilize covalently the subunits of a complex have been developed. These procedures give interesting results but also have strong limitations (Farmer et al., Biological Mass Spectrometry 20:796-800, 1991; Farmer et al., J. Mass Spectrom. 33:697-704, 1998). Among these limitations, the low efficiency of the crosslinking stabilization protocol used and the impossibility to detect the intact protein complexes in the high-molecular range (higher than 200 kDa) are particularly noteworthy.

Recently, using the combination of specially developed MALDI high-mass detection and a new crosslinking protocol, Nazabal et al. were able to analyze protein-protein interactions with a higher level of complexity and a improved sensitivity in a high-mass range (Nazabal, A. et al., Anal. Chem. 78:3562-3570, 2006; WO 2006/116893).

The mentioned analytical methods have never been applied to the quantitative analysis of antibody or other therapeutic protein aggregates because MALDI mass spectrometry is cumulating three major disadvantages: 1) the laser used for the ionization disrupts the non-covalent interactions of the aggregates; 2) detection sensitivity is reduced or inexisting in the high-mass range; and 3) MALDI mass spectrometry is not considered a quantitative tool. Only one study by Farmer et al. (J. Mass Spectrom. 30:1245-1254, 1995) proposed a basis for the quantitative analysis of crosslinked oligomeric complexes using MALDI mass spectrometry. The method proposed the use of a correction factor to compensate the use of standard detection in the experiments. The use of standard detection systems leads to detection limitations in the higher mass range; limitations that may be compensated by a correction factor calculated for the 30-150 kDa range. This correction factor for detection efficiency is only applicable when using the same type of instrument and for exactly the same experimental set-up, extremely limiting this method for the quantitative analysis and making it difficult to apply.

In WO 2006/116893 (Eidgenössische Technische Hochschule Zürich) a mass spectrometric method is proposed wherein intact ions of undigested, unfragmented covalently stabilized supramolecular target-ligand complexes are analyzed with matrix assisted laser desorption ionization (MALDI). The method is illustrated by the analysis of antibody-antigen complexes and other protein-protein complexes such as complexes between CDC42 and *Salmonella* outer protein E, but has not been used for the analysis of self-aggregation of an antibody or a therapeutic protein. In addition, this method has never been used for quantitative analysis of the amount of protein complex formed.

SUMMARY OF THE INVENTION

It is an object of the present invention to provide a method of determination of the amount of aggregation of therapeutic proteins, for example antibodies, drugs or drug candidates, by crosslinking aggregates to form covalently stabilized aggregates in either purified multi-component samples or heterogeneous biological matrices and subsequent analysis of the obtained mixture of monomeric and aggregated therapeutic proteins with MALDI ToF mass spectrometry equipped for high-mass detection without digestion or fragmentation of the sample.

In particular, the present invention provides a method of determination of the amount of aggregation by measuring intact ions of undigested, unfragmented therapeutic protein aggregates together with intact ions of undigested, unfragmented monomeric therapeutic proteins using mass spectrometry comprising the steps of:

(a) contacting a mixture of monomeric and non-covalently aggregated therapeutic proteins with a crosslinking reagent to form covalently stabilized therapeutic protein aggregates;
(b) analyzing the intact ions formed by High-Mass MALDI ToF mass spectrometry equipped with a high-mass detector;
(c) determining directly the amount of aggregation in the therapeutic protein sample by comparing the mass peaks with a pre-established calibration curve.

The present invention further provides the use of this method as a versatile tool in various applications such as drug development, characterization of therapeutic proteins, for example antibodies, drugs or drug candidates, in manufacturing processes, and in protein quality control including automated and/or high throughput applications.

This method for the quantitative analysis does not require any correction factor dependent on instrument or experimental conditions to compensate the saturation effect affecting the detection of high molecular weight ions (dimers versus monomer). In the present invention a simple calibration curve gives a direct access to the exact quantity of aggregates present in the sample.

BRIEF DESCRIPTION OF THE FIGURES

FIG. 1: Direct determination of the amount of aggregation in antibody samples.
High-Mass MALDI ToF analysis of antibody monomer (Ab) and dimer [Ab.Ab] mixture after stabilization using cross-linking and High-Mass MALDI mass spectrometry. The mixture contains increasing quantities of antibody dimers (A. 0%, B. 10%, C. 20%, D. 30%, E. 50%, F. 80%).
G. Calibrating curve obtained by plotting $R_{iD}/(R_{im}+R_{iD})$ as a function of the % of antibody dimer present in the sample. $R_{iD}$ is the integration of the antibody dimer peak and $R_{im}$ is the integration of the antibody monomer peak.

FIG. 4: Limit of sensitivity for the aggregate detected and repeatability.
A. Monomeric sample of TN 300707 analyzed by High-Mass MALDI ToF mass spectrometry after crosslinking.
B. Partially aggregated sample of TN 300707 analyzed by High-Mass MALDI ToF mass spectrometry after crosslinking.
C. Calibrating curve obtained by plotting $R_{iD}/(R_{im}+R_{iD})$ as a function of the % of dimer present in the sample. $R_{iD}$ is the integration of the dimer peak and $R_{im}$ is the integration of the monomer peak. The amount of the protein dimer was calculated and shows an aggregation rate of 4.47%.
D. The experiment was repeated 10 times to address the accuracy of the quantitative method. The results indicate a high repeatability (4.47±0.08%) among the 10 individual samples tested.

DETAILED DESCRIPTION OF THE INVENTION

The present invention relates to a method of analyzing the amount of aggregation of therapeutic proteins, for example antibodies, drugs or drug candidates, in either purified multicomponent mixtures or heterogeneous biological matrices with high sensitivity and accuracy using the combination of High-Mass MALDI ToF mass spectrometry and crosslinking chemistry for a robust and routine analysis.

In particular the method of the present application allows the analysis of intact therapeutic protein (antibody or other therapeutic protein such as a drug or a drug candidate including a potential drug) aggregates with high sensitivity and accuracy by first crosslinking specifically the non-covalently bound protein aggregates and subsequently subjecting it to MALDI ToF mass spectrometry using sensitive high-mass detection with no digestion or fragmentation step. The amount of aggregation in the sample is determined directly from the MALDI mass spectrum obtained using a standard calibration curve with no need for correction factor or other instrument adjustment. The present invention demonstrates that it is possible to establish a correlation between the amount of aggregation in a therapeutic protein sample and the surface area of the peaks detected for the monomeric form and the aggregated form(s) in the sample analyzed by High-Mass MALDI mass spectrometry. Such quantification does not require any correction factor to compensate the limit of detection of the mass spectrometer, taking benefits of the use of special high-mass detection system giving low saturation and high-sensitivity in the high-mass range (higher than 200 kDa). The present invention also demonstrates the possibility of quantification of low amount of aggregates (lower than 5%) with high accuracy taking benefits of the sensitivity of high-mass detection system and high efficiency of the cross-linking protocol developed.

In a specific embodiment the therapeutic protein aggregates are analyzed in either purified multi-component samples or heterogeneous biological matrices with no digestion or fragmentation step.

In a further specific embodiment, the antibody aggregates represent a non-covalent complex of two antibodies (antibody dimer), three antibodies (antibody trimer) or multimer of antibodies. Further therapeutic proteins considered are drugs or drug candidates including potential drugs composed of a chain of amino acids. The therapeutic protein aggregates represent a non-covalent complex of two therapeutic proteins (dimer), three therapeutic proteins (trimer) or multimers of therapeutic proteins. Thus, the antibody and other therapeutic protein aggregates formed result from antibody-antibody interactions or protein-protein interactions, respectively.

The method of the present invention provides for a direct mass analysis of therapeutic protein aggregates with no digestion or fragmentation, and thus also includes the ability to recognize variants of therapeutic protein aggregates and to elucidate their amount within the sample.

The use of the method of the present invention allows not only a direct quantification of the amount of aggregation, but also the determination of the stoichiometry of the different aggregated species present in the sample and also, the physical properties of the interaction (non-covalent or covalent interaction), all in the same experiment. If the interaction is of covalent or partially covalent nature, the corresponding covalently bound aggregates are detected by High-Mass MALDI ToF mass spectrometry already before contacting the mixture comprising the therapeutic proteins with a crosslinking reagent or a crosslinking reagent mixture.

The invention itself will best be understood from the following description of the preferred embodiments. It is understood that those skilled in the art may conceive modifications and/or variations to the specific embodiments shown and described herein. Any such modifications or variations that fall within the purview of this description are intended to be included therein as well. The description of preferred embodiments and best mode of the invention known to the applicant at the time of filing the application are presented and are intended for the purposes of illustration and description. It is not intended to be exhaustive or to limit the invention to the precise form disclosed, and many modifications and variations are possible in the light of the teachings above and below. The embodiments demonstrate the principles of the invention and its practical applications and enable others skilled in the art to best utilize the invention in various embodiments and with various modifications as are suited to the particular use contemplated.

The method of the present invention allows the direct determination of the amount of aggregation of therapeutic protein samples, e.g. from either purified samples such as pharmaceutical samples or heterogeneous biological matrices, using High-Mass MALDI ToF mass spectrometry and crosslinking chemistry.

The method of the present invention is based on the finding that the analysis of therapeutic protein aggregates is possible after crosslinking, e.g. in either a purified pharmaceutical sample or in heterogeneous biological matrices. High-Mass MALDI mass spectrometry allows the direct determination of the amount of aggregation in the sample. There is a correlation between the surface area of the peaks detected by MALDI mass spectrometry equipped with high-mass detection system and the proportion of the aggregated form of the therapeutic protein present in the sample.

The present invention provides a direct method for determining the amount of aggregation of therapeutic proteins and comprises the steps of:
(a) contacting a mixture of monomeric and of non-covalently aggregated therapeutic proteins with a crosslinking reagent (including a crosslinking reagent mixture) to form covalently stabilized therapeutic protein aggregates;
(b) analyzing the intact ions formed from the protein monomers and aggregates of step (a) by High-Mass MALDI ToF mass spectrometry equipped with a high-mass detector;
(c) determining directly the amount of aggregation by comparing the mass peaks with a pre-established calibration curve.

The calibration curve is obtained by analyzing pre-formed mixtures with known amounts of monomers and crosslinked aggregates (dimers, trimers, etc.) under identical reaction conditions by High-Mass MALDI ToF mass spectrometry and plotting peak areas for monomer and aggregates as a function of the composition of the pre-formed mixture. By integrating the surface area of the monomeric and aggregated peaks observed in the mass spectrum, a standard curve can be established by plotting $R_{iD}/(R_{im}+R_{iD})$ as a function of the amount of aggregation in the sample. This standard curve is then used to establish directly the amount of aggregation of unknown samples. In particular, the amount of aggregation is established based on the total surface area of the peaks corresponding to monomeric and aggregated therapeutic protein present in the same mass spectrum. The present invention provides a direct method to analyze the amount of therapeutic protein aggregates in a pharmaceutical sample with high detection sensitivity. The method provides the determination of the amount of aggregates from 2 to 100% in samples with an accuracy of 0.1%.

If the crosslinking step is omitted the High-Mass MALDI ToF mass spectrometry of a therapeutic protein sample corresponds to a sample containing monomers without aggregates since the non-covalently bound aggregates decay into monomers under the conditions of mass spectrometry.

More particularly, the method of determining the amount of aggregation by measuring intact ions of an undigested, unfragmented therapeutic protein monomers and aggregates comprises:
(a) obtaining a first sample comprising therapeutic protein monomer and non-covalently bound therapeutic protein aggregate(s);
(b) contacting said first sample with a crosslinking reagent or crosslinking reagent mixture to obtain a second sample comprising therapeutic protein monomer and covalently stabilized therapeutic protein aggregate(s),
(c) mixing said second sample with a matrix solution to obtain a sample/matrix mixture;
(d) depositing said sample/matrix solution on a substrate, thereby forming a homogeneous, thin layer;
(e) illuminating the substrate with radiation from a laser whereby said therapeutic protein monomer and covalently stabilized therapeutic protein aggregate(s) are desorbed and intact ions are generated;
(f) mass separating and detecting said intact ions of the undigested, unfragmented therapeutic protein monomer and covalently stabilized therapeutic protein aggregate(s) using a mass separation and a high-mass detection system;
(g) determining the surface area of the peaks detected for the monomeric form and the aggregated form(s) of the therapeutic protein;
(h) plotting the value of these surface area on a pre-established calibration curve;
(i) determining from the calibration curve the amount of aggregation of the sample.

If desired, to determine the amount of covalent aggregation of therapeutic proteins in an untreated mixture the intact ions in the mixture are further analyzed by High-Mass MALDI ToF mass spectrometry under identical conditions before contacting the mixture with a crosslinking reagent or a crosslinking reagent mixture. This allows to differentiate between covalent and non-covalent aggregation.

As used herein, the term "obtaining" does not include any procedure practiced on the human or animal body, but means any other procedure of obtaining a sample comprising a therapeutic protein, e.g. from manufacturing processes or from biological matrices, such as cell cultures and isolated samples from animals including man, as is more explained hereinbelow.

As used herein, the term "therapeutic protein aggregate" and "antibody or other therapeutic protein aggregate" refers to non-covalent interaction arising from specific or non-specific binding of two antibody molecules or two therapeutic protein molecules (dimer); three antibody molecules or three therapeutic protein molecules (trimer) or of a multimer composed of four, five, six or more monomers of antibody molecules or other therapeutic protein molecules, wherein other therapeutic drug molecules are, for example, drugs or drug candidates including potential drugs. For the purpose of clarity, "aggregate" means "self-aggregate" if only one kind of therapeutic protein molecule is present. If two or more different therapeutic proteins are present in a sample, "aggregate" comprises any kind of aggregate, i.e. aggregates between different therapeutic proteins and self-aggregates.

As used herein, the term "amount of aggregation" refers to the portion of the therapeutic protein aggregated in the sample. This amount of aggregation may be expressed as a ratio of monomer to dimer to trimer to multimer, as a percentage of a monomer or of an aggregate in the total mixture of monomers and aggregates, or by another relative indication of the corresponding amounts of monomers and aggregates.

As used herein, the term "High-Mass MALDI mass spectrometry" refers to analysis using matrix assisted laser desorption ionization mass spectrometer instrument specially modified to enhance the sensitivity of detection of ions in the high-molecular range, e.g. ranging from about 5 kDa to about 100 MDa, more specifically from about 10 kDa to about 20 MDa, most preferably from about 10 kDa to about 10 Mda, whatever the technology applied to perform this enhancement is.

As used herein, the term "intact ions" refers to charged molecules created for mass analysis from the covalently stabilized aggregates without proteolysis, degradation, or dissociation of the therapeutic protein before or during mass analysis.

As used herein, the term "covalently stabilized therapeutic protein aggregate" or "covalently stabilized antibody or other therapeutic protein aggregate" refers to aggregates as defined above, which have been crosslinked by any known or as yet undiscovered means without disturbing the stoichiometry of the aggregate.

As used herein, the term "purified pharmaceutical sample" refers to any sample containing a heterogeneous or homogeneous mixture of antibodies, proteins, polypeptides, glycopolypeptides, phosphopolypeptides, peptidoglycans, polysaccharides, peptidomimetics, lipids, carbohydrates, polynucleotides or organic compounds, which has been purified in part or completely.

As used herein, the term "heterogeneous biological matrices" refers to any crude reaction mixtures including mixtures obtained from dissolution of a solid material such as a tissue, cells, or a cell pellet; biological fluid such as urine, blood, saliva, amniotic fluid, or an exudate from a region of infection or inflammation; a cell extract, or biopsy sample; or mixtures obtained from a living source, for example, an animal such as a human or other mammal, a plant, a bacterium, a fungus or a virus.

As used herein, the term "high or higher mass" with reference to therapeutic protein aggregates refers to a mass higher than about 10 kDa, e.g. ranging from about 10 kDa to about 100 MDa, more specifically from about 20 kDa to about 20 MDa, most preferably from about 30 kDa to about 10 MDa.

As used herein, the term "analyze" means to identify or detect the presence, absence or change of, or determine the identity of such covalently stabilized therapeutic protein aggregates as intact ions.

As used herein, the term "high throughput" means to conduct more than one analysis per day, more specifically several per day, most preferably hundreds per day.

As used herein, the term "high sensitivity of aggregates detection" refer to the ability of the method to detect low amount of therapeutic protein aggregates.

The method of the present invention allows the analysis of the amount of aggregation of both purified or crude samples, i.e. biological samples, which may or may not have undergone some purification but still may contain extraneous contaminants, with high accuracy (e.g. around 0.1%), high sensitivity (e.g. around 2%) and high signal-to-noise ratio. Thus the amount of aggregation of high molecular weight therapeutic protein aggregates from contaminated samples, which is otherwise difficult to analyze due to the presence of mixtures, contaminants, or impurities is made possible by the method of the present invention and further may be made amenable to automation as desired in large-scale processes. This may include the use of software for interpretation of the data as well as robotics for the control of the sample preparation and/or analysis.

The present invention further provides the use of this method in various applications such as product development, characterization of therapeutic proteins in manufacturing processes, and therapeutic protein quality control including automated and/or high throughput applications.

In practicing an embodiment of the method of the present invention, a sample containing the non-covalently bound therapeutic protein aggregates to be analyzed is first subjected to crosslinking conditions using e.g. amine reactive crosslinking chemical reactions for stabilizing the aggregates prior to High-Mass MALDI mass spectrometric analysis. Typical crosslinking reagents useful for the method of the invention are such reagents as listed in patent application WO 2006/116893. Possible crosslinking reagents include both homo- and hetero-multifunctional reagents, and comprise imidoesters, N-hydroxysuccinimide(succinimidyl)ester, maleimides, haloacetates, pyridyl disulfides, hydrazides, carbodiimides, aryl azides, isocyanates, vinyl sulfones, and the like. Illustrative of the crosslinking reaction of a succinimidyl ester is the scheme below, wherein R is a residue comprising a further reactive group, e.g. another succinimidyl ester function or a residue bearing iodine, and R'—NH$_2$ indicates an accessible amino group in the protein:

Typically, a solution containing a crosslinking reagent of choice is added to a sample containing the aggregates followed by incubation for a specified time, e.g. 1 to 60 minutes, preferably around 30 minutes, at around room temperature, 0° C. or up to 40° C., to ensure completion of the reaction. Typical crosslinkers include homo- and hetero-multifunctional crosslinking agents. Preferred crosslinking reagents for this analysis are mixtures composed of at least one of the following crosslinkers: Disuccinimidyl tartrate, octanedioic acid bis(3-sulfo-N-hydroxysuccinimide)ester, iodoacetic acid N-hydroxysuccinimide ester, disuccinimidyl 3,3'-dithiopropionate, octanedioic acid di-N-hydroxysuccinimide ester, and ethylene glycol bis(succinimidyl succinate).

The reaction conditions of the crosslinking step must be carefully chosen in order not to cause crosslinking of non-aggregated monomers.

After completion of the crosslinking reaction, the obtained liquid mixture is used in a High-Mass MALDI mass spectrometric setup as described above.

While the amount of aggregation can be determined in a purified sample, e.g. a pharmaceutical sample, it is also possible to determine the amount of aggregation in complex biological matrices.

After completion of the crosslinking reaction, the liquid is intended to be used in any mass spectrometry setup, preferably a MALDI MS setup. In a preferred embodiment, an aliquot, e.g. 1 microliter, of the sample containing therapeutic protein monomer and the now covalently stabilized aggregate (s) is mixed with an aliquot, e.g. 1 microliter, of a matrix solution to obtain a sample/matrix-mixture or spotted directly on a plate covered with a thin layer of matrix or other MALDI sample deposition techniques, as known by those familiar in the art. Typical matrix solutions for use in the methods disclosed herein have a sufficient absorption at the wavelength of the laser to be used in performing desorption and ionization, are liquid at around room temperature (25° C.) and can form a vitreous or glassy solid. Among the preferred matrices are those mentioned to be preferred in patent application WO 2006/116893. Particularly preferred is sinapinic acid (3-(4-hydroxy-3,5-dimethoxyphenyl)-prop-2-enoic acid). Materials of relatively low volatility are preferred to avoid rapid evaporation under conditions of vacuum during MS analyses. Preferably the liquid has an appropriate viscosity to facilitate dispensing of microliter to nanoliter volumes of matrix, either alone or mixed with a sample solution. Preferably, any liquid (s) used in preparation of the solution are removed by drying the sample/matrix-mixture before analysis to form a homogenous "solid solution", i.e. comprising the analyte complexes distributed throughout the matrix. In a preferred embodiment, the matrix solution contains, for example, sinapinic acid (around 10 mg/mL) in a solution containing acetonitrile, water and trifluoroacetic acid. Due to the stabilization of aggregates achieved by the crosslinking step it is not necessary to undergo the laborious process of optimizing "soft" conditions such as matrix solutions without organic solvent or soft laser analysis (i.e. low laser powers used or first shot analysis).

While the above described preferred embodiment involves using dried liquid solutions, other methods such as liquid MALDI, online AP-MALDI, solid phase preparation, and other sample preparation techniques can be used as they are well known in the art.

In a preferred embodiment, the ion particles generated are extracted for analysis by the mass analyzer in a delayed fashion prior to separation and detection in a mass analyzer. Preferably, the separation formats include, but are not limited to, linear or reflectron time-of-flight (ToF), with linear and nonlinear fields, for example, curved field reflectron; single or multiple quadrupole; single or multiple magnetic or electric sector; Fourier transform ion cyclotron resonance (FTICR); or ion trap mass spectrometers, most preferably, linear Time of Flight (ToF).

While a ion conversion dynode (ICD) is preferred, other known detectors which are sensitive to high-mass ions and thus are able to detect chemically stabilized multicomponent ions may be used, which include, but are not limited to, superconducting tunnel junction (STJ) detectors, optically decoupled, amplified, or specially coated electron multipliers or MCP's, and other cryodetectors or sensitive high-mass detectors, as they are well known in the art.

EXAMPLES

Mass Spectrometry: All the mass measurements were performed on MALDI ToF mass spectrometer Reflex IV (Bruker, Bremen) equipped with a high-mass retrofit detector system (HM1, CovalX, Zürich, Switzerland). CovalX HM1 high-mass retrofit system is designed to optimize the detection of high molecular weight molecular ions in the 5-1500 kDa range. CovalX HM1 high-mass retrofit system can be installed on every standard MALDI-TOF mass spectrometer.

Example 1

Use of Chemical Crosslinking and High-Mass MALDI Mass Spectrometry for the Determination of Aggregation Amount of the Therapeutic Antibody Candidate Hab-32

Figure 1:
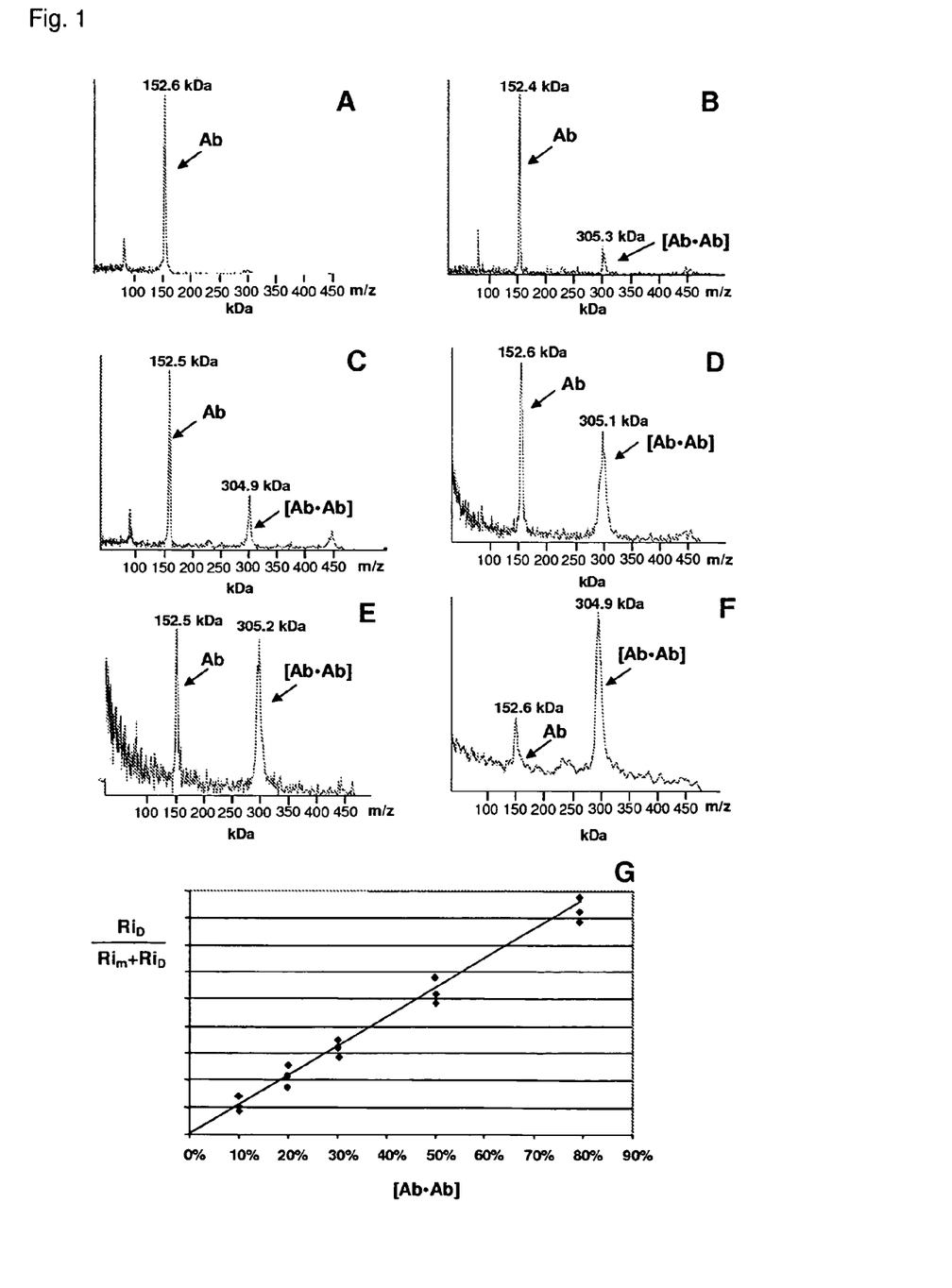

Hab-32 is a drug-antibody candidate making tumor cells more vulnerable to chemotherapy and radiation and slowing tumor cell growth. Purified samples of Hab-32 monomer and dimer are prepared using size exclusion chromatography. The different fractions of the size exclusion chromatography are submitted to crosslinking using a mixture of 1:1:1 octanedioic acid bis(3-sulfo-N-hydroxysuccinimide)ester, disuccinimidyl 3,3'-dithio-propionate and disuccinimidyl glutarate (200 µg/mL). After incubation at 25° C. for 45 min, mixed samples containing different amounts of monomer and dimer of Hab-32 in known concentration are prepared. The samples are analyzed using High-Mass MALDI ToF mass spectrometry (HM1, CovalX, Zürich, Switzerland) (FIGS. 1A, B, C, D, E, F). In each spectrum, two peaks are detected corresponding to Hab-32 monomer and Hab-32 dimer. From these spectra, the surface areas of the peaks detected ($R_{iD}/(R_{im}+R_{iD})$) are plotted as a function of the % of aggregation. $R_{iD}$ is the surface area of the peak dimer, $R_{im}$ is the surface area of the peak monomer. The calibration curve obtained indicates the correlation between the percentage of the aggregated antibody present in the sample and the surface area of the peak detected by High-Mass MALDI ToF MS. The protein concentration for each sample is 1 µM with a volume of 10 µL. 1 µL of 1 mg/mL crosslinking mixture is used to stabilize the aggregates before High-Mass MALDI ToF analysis. Samples are prepared by mixing 1 µL of aggregates solution with 1 µL of sinapic acid (10 mg/mL in 70% acetonitrile:30% water:0.1% trifluoroacetic acid) and spotting 1 µL using dried droplet technique.

Example 2

Figure 2:
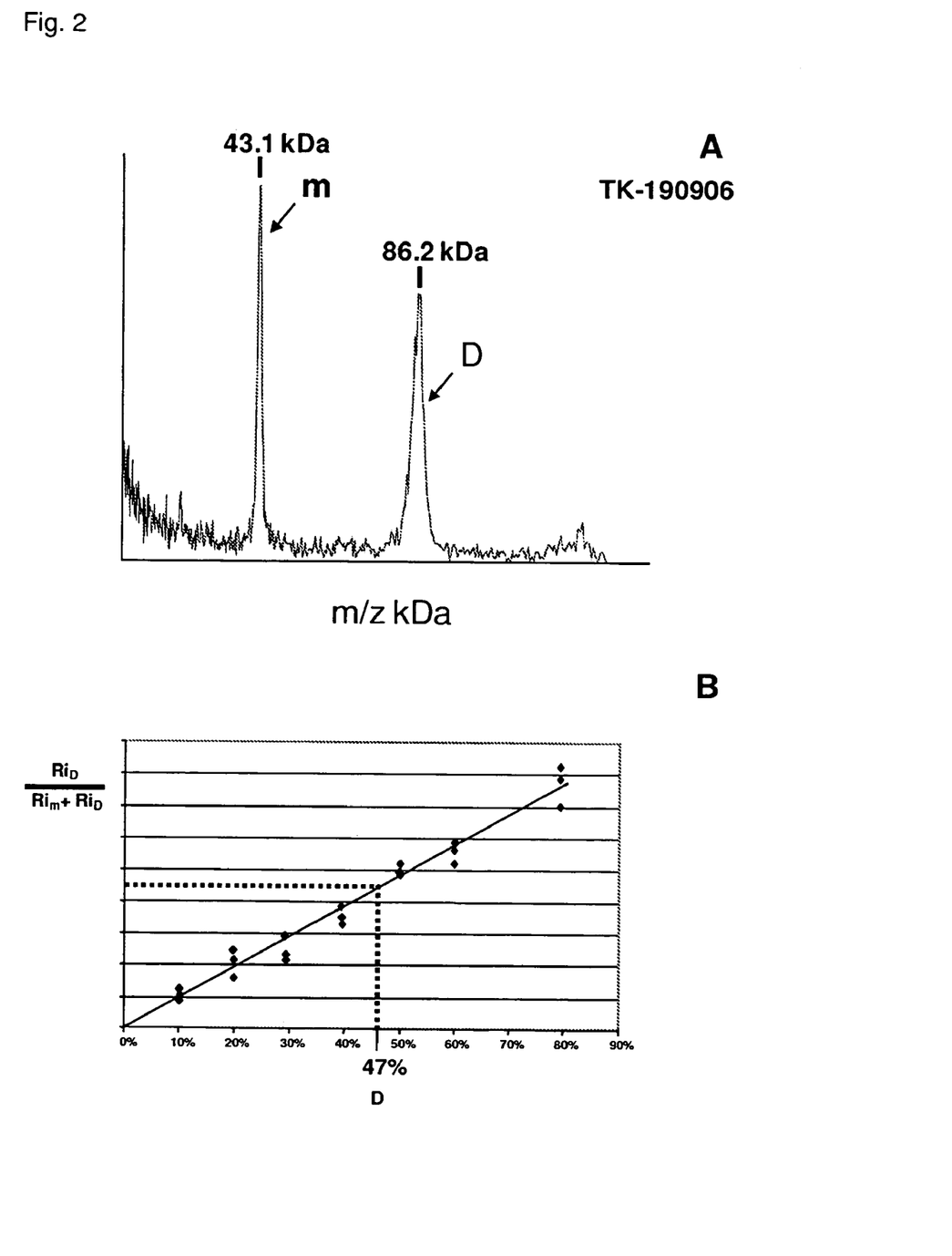
FIG. 2: Determination of the amount of aggregation in a sample containing the therapeutic protein (drug candidate) TK-190906.
A. Analysis of aggregates of TK-190906 by High-Mass MALDI mass spectrometry after crosslinking. m=monomer, D=dimer.
B. Using a calibration curve, the amount of aggregation for the aggregated sample TK-190906 is determined.

Determination of the Amount of Aggregation in a Sample Containing Aggregates of the Therapeutic Protein TK-190906 Using Chemical Crosslinking and High-Mass MALDI TK-190906 is a drug candidate developed for its effect on various physiologic pathways involving tyrosine kinase. This example demonstrates the determination of the amount of aggregation directly from a non-purified sample of the therapeutic protein TK-190906. The sample containing the protein TK-190906 is directly submitted without previous size exclusion chromatography to the crosslinking reaction using a 3:1:1 mixture of disuccinimidyl tartrate, iodoacetic acid N-hydroxysuccinimide ester and disuccinimidyl 3,3'-dithio-propionate (200 µg/mL, 25° C., 45 min). After High-Mass MALDI mass spectrometry analysis, the dimer of the therapeutic protein TK-190906 is clearly detected with m/z 86.2 kDa (FIG. 2A). From the calibration curve obtained as in Example 1, the amount of aggregation can be directly determined in the sample. The reactions involve 10 µL of 500 nM of TK-190906 sample. For the MS analysis, samples are prepared using 1 µL of solution mixed with 1 µL of sinapinic acid (10 mg/mL in 70% acetonitrile:30% water:0.1% trifluoroacetic acid) and spotting 1 μL using dried droplet technique.

Example 3

Figure 3:
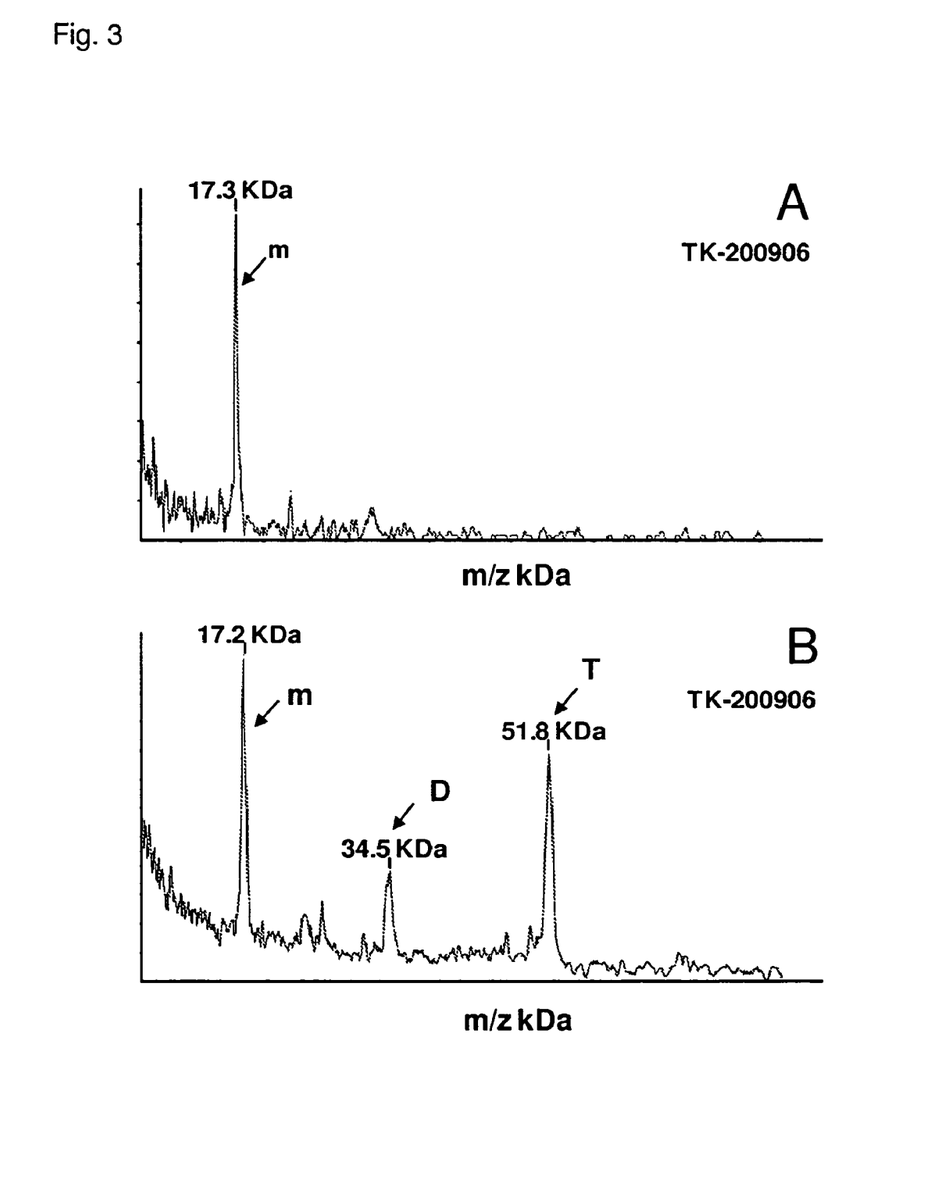
FIG. 3: Mass spectral results from a complex sample containing therapeutic protein TK-200906 aggregates.
A. A monomeric sample of TK-200906 is analyzed by High-Mass MALDI ToF mass spectrometry after crosslinking.
B. A partially aggregated sample of TK-200906 is analyzed by High-Mass MALDI ToF mass spectrometry after crosslinking. The amount of the protein dimer (D) and trimer (T) formation is calculated directly from the surface area of the peaks present in the mass spectrum. Values found are 49% monomer, 16% dimer and 35% trimer.

Determination of the Amount of Aggregation for the Protein LK-200906 Using Crosslinking Stabilization and MALDI Mass Spectrometry LK-200906 is a drug candidate evaluated for its effect on the MAPk pathways. This example demonstrates the protein LK-200906 under monomeric conditions (FIG. 3A) and in aggregated conditions (FIG. 3B). In the spectra of aggregates a dimer and a trimer of the protein LK-200206 is detected at m/z=34.5 kDa and m/z=51.8 kDa. The reactions involve 10 μL of 500 nM of LK-200206 submitted to a crosslinking reaction using a 3:1:1:1 mixture of disuccinimidyl tartrate, iodoacetic acid N-hydroxysuccinimide ester, disuccinimidyl 3,3'-dithiopropionate and ethylene glycol bis(succinimidyl succinimate) (200 μg/mL, 25° C., 45 min). The amount of aggregation for the sample is determined considering the surface area of the peaks for the monomer, the dimer and the trimer as 100%. The analysis indicates that the aggregated sample of LK-200906 is containing 49% of the monomeric form, 16% of the dimeric form and 35% of the trimeric form.

Example 4

Figure 4:
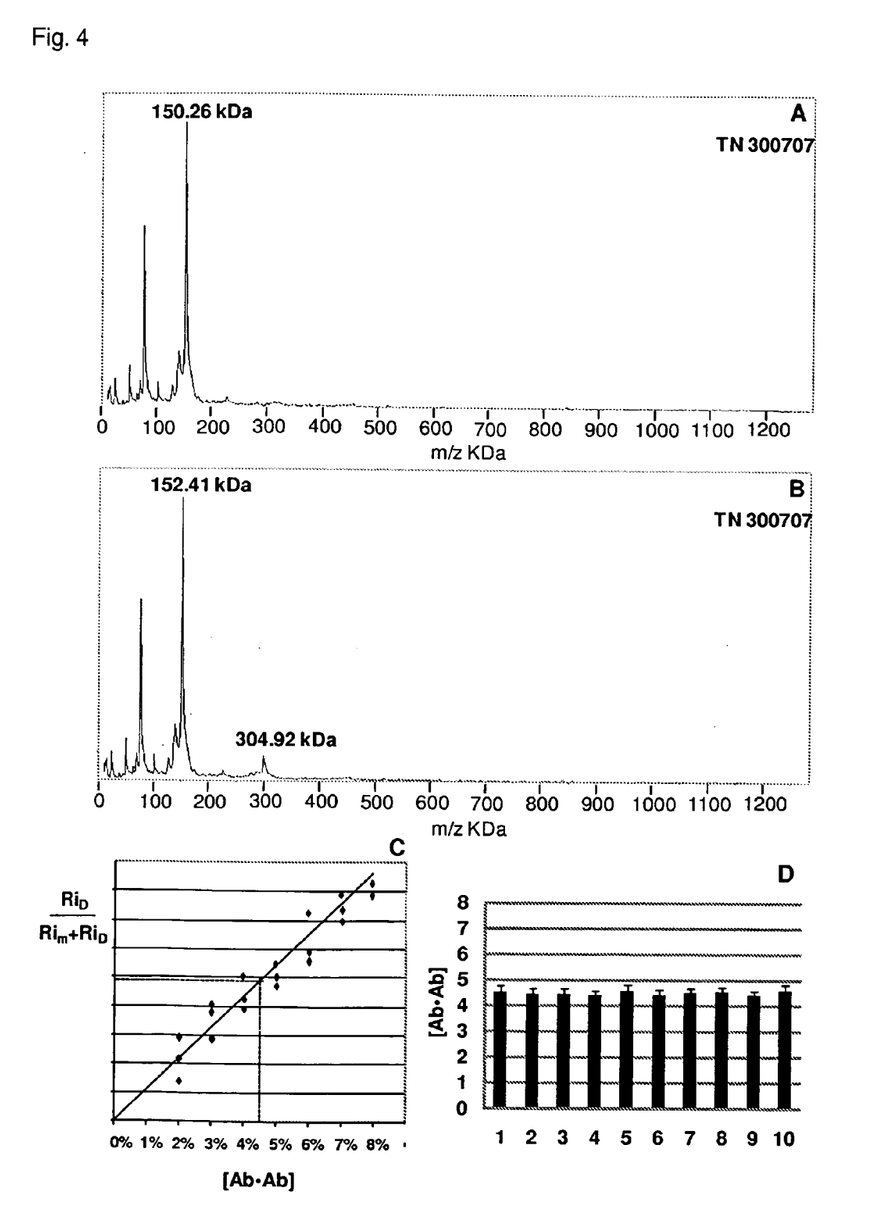

Determination of the Amount of Aggregation for the Antibody TN 300707 Using Crosslinking Stabilization and MALDI Mass Spectrometry TN 300707 is a therapeutic antibody candidate evaluated for treatment of Cardiopulmonary Bypass. This example demonstrates the High-Mass MALDI analysis of a sample containing a low amount of aggregates. Before treatment with crosslinking reagents, no dimer of the protein TN 300707 is detected (FIG. 4A). After crosslinking, a dimer of TN 300707 is detected with m/z=304.92 (FIG. 4B). The analysis involves 10 μL of 500 nM of TN 300707 submitted to crosslinking reaction using a 3:1:1:1 mixture of disuccinimidyl tartrate, iodoacetic acid N-hydroxysuccinimide ester, disuccinimidyl 3,3'-dithiopropionate and ethylene glycol bis(succinimidyl succinimate) (200 μg/mL, 25° C., 45 min). The amount of aggregation for the sample is determined considering the surface area of the peaks for the monomer and the dimer peak for the crosslinking experiment and compared to a pre-established calibration curve (FIG. 4C). The analysis indicates that the sample of TN 300707 contains 4.47% of dimer. The same experiment has been repeated 10 times indicating a high accuracy of the analysis with a dimer value of 4.47%±0.08.

The invention claimed is:

1. A method for the determination of the amount of self-aggregation of therapeutic proteins comprising the steps of:
    (a) contacting a mixture of monomeric and of non-covalently aggregated therapeutic proteins with a crosslinking reagent or a crosslinking reagent mixture of at least one member selected from the group consisting of imidoesters, N-hydroxysuccinimide esters, maleimides, haloacetates, pyridyl disulfides, hydrazides, carbodiimides, aryl azides, isocyanates, and vinyl sulfones, to form a crosslinked mixture of covalently stabilized therapeutic protein aggregates;
    (b) analyzing the intact ions formed from the protein monomers and aggregates in the crosslinked mixture of step (a) by High-Mass MALDI ToF mass spectrometry equipped with a high-mass detector giving low saturation and high sensitivity in a mass range higher than 200 kDa; and
    (c) determining directly the amount of aggregation by comparing the mass peaks with a pre-established calibration curve.

2. A method for the determination of the amount of self-aggregation of therapeutic proteins comprising the steps of:
    (a) obtaining a first sample comprising therapeutic protein monomer and non-covalently bound therapeutic protein aggregate(s);
    (b) contacting said first sample with a crosslinking reagent or crosslinking reagent mixture of at least one member selected from the group consisting of imidoesters, N-hydroxysuccinimide esters, maleimides, haloacetates, pyridyl disulfides, hydrazides, carbodiimides, aryl azides, isocyanates, and vinyl sulfones, to obtain a second sample comprising therapeutic protein monomer and covalently stabilized therapeutic protein aggregate(s) in a crosslinked mixture;
    (c) mixing said second sample with a matrix solution to obtain a sample/matrix mixture;
    (d) depositing said sample/matrix solution on a substrate, thereby forming a homogeneous, thin layer;
    (e) illuminating the substrate with radiation from a laser whereby said therapeutic protein monomer and covalently stabilized therapeutic protein aggregate(s) are desorbed and intact ions are generated;
    (f) mass separating and detecting said intact ions of the undigested, unfragmented therapeutic protein monomer and covalently stabilized therapeutic protein aggregate(s) using a mass separation and a high-mass detection system giving low saturation and high sensitivity in a mass range higher than 200 kDa;
    (g) determining the surface area of the peaks detected for the monomeric form and the aggregated form(s) of the therapeutic protein;
    (h) plotting the value of these surface area on a pre-established calibration curve; and
    (i) determining from the calibration curve the amount of aggregation of the sample.

3. The method according to claim 1 or 2, wherein the calibration curve is established by analyzing aggregated therapeutic protein samples with known amount of aggregation.

4. The method according to claim 1, wherein the amount of aggregation is established based on the total surface area of the peaks corresponding to monomeric and aggregated therapeutic proteins present in the same mass spectrometry spectrum.

5. The method according to claim 2, wherein the intact ions in the mixture comprising the therapeutic proteins are further analyzed by High-Mass MALDI ToF mass spectrometry equipped with a high-mass detector before contacting the mixture with a crosslinking reagent or a crosslinking reagent mixture in order to determine the amount of covalent aggregation.

6. The method according to claim 2, wherein the therapeutic protein aggregates are analyzed in purified multicomponent samples or in heterogeneous biological matrices.

7. The method according to claim 2, wherein the therapeutic protein is an antibody.

8. The method according to claim 2, wherein the therapeutic protein is a drug or a drug candidate.

9. The method according to claim 1, wherein the crosslinking reagent is one reagent or a mixture of crosslinking reagents selected from disuccinimidyl tartrate, octanedioic acid bis(3-sulfo-N-hydroxysuccinimide) ester, iodoacetic acid N-hxdroxysuccinimide ester, disuccinimidyl 3,3'-dithiopropionate, octanedioic acid di-N-hydroxysuccinimide ester, disuccinimidyl glutarate and ethylene glycol bis(succinimidyl succinate).

10. The method according to claim 2, wherein the high-mass detector is an ion conversion dynode (ICD) detector.

11. The method according to claim 2, wherein the amount of aggregation is established based on the total surface area of the peaks corresponding to monomeric and aggregated therapeutic proteins present in the same mass spectrometry spectrum.

12. The method according to claim 2, wherein the crosslinking reagent is one reagent or a mixture of crosslinking reagents selected from disuccinimidyl tartrate, octanedioic acid bis(3-sulfo-N-hydroxysuccinimide) ester, iodoacetic acid N-hxdroxy-succinimide ester, disuccinimidyl 3,3'-dithiopropionate, octanedioic acid di-N-hydroxy-succinimide ester, disuccinimidyl glutarate and ethylene glycol bis(succinimidyl succinate).

* * * * *